(12) United States Patent
Windle

(10) Patent No.: US 6,638,715 B1
(45) Date of Patent: Oct. 28, 2003

(54) METHODS AND COMPOSITIONS FOR EXTENDED AND SUPER-EXTENDED DNA AND HYBRIDIZATION MAPPING

(75) Inventor: Bradford E. Windle, San Antonio, TX (US)

(73) Assignee: CTRC Research Foundation, San Antonio, TX (US)

( * ) Notice: Subject to any disclaimer, the term of this patent is extended or adjusted under 35 U.S.C. 154(b) by 0 days.

(21) Appl. No.: 08/361,328

(22) Filed: Dec. 21, 1994

Related U.S. Application Data

(63) Continuation-in-part of application No. 08/264,802, filed on Jun. 23, 1994, now Pat. No. 5,707,797, which is a continuation-in-part of application No. 08/002,781, filed on Jan. 8, 1993, now abandoned.

(51) Int. Cl.[7] .............................. C12Q 1/68; C07H 21/00
(52) U.S. Cl. ......................... 435/6; 536/23.1; 536/25.3; 536/25.4
(58) Field of Search .......................... 435/6, 174, 320.1, 435/820; 536/22.1, 23.1, 24.1, 24.3–24.33, 25.4–25.42, 25.3; 935/1, 6, 78

(56) References Cited

PUBLICATIONS

Washizer et al., IEEE Transactions on Industry Applications, vol. 26, No. 6, pp. 1165–1172, 1990.*
Biochemistry, by A.L. Lehninger (Worth Publishers, Inc., New York, NY, 1970) pp 635–658.*
Windle et al. (1993) Cancer Genetics and Cytogenetics, vol. 66, No. 2, Abstract #16, p. 144.*
Matsumoto et al. (1981) Journal of Mol. Biol., vol. 152, pp 501–516.*
Kanda et al. (1983) Proc. Nat'l Acad Sci (USA) vol. 80, pp 4069–4073.*
Pinkel et al. (1986) Proc. Nat'l Acad Sci (USA), vol. 83, pp 2934–2938.*
Parra et al. (1993) Nature Genetics, vol. 5, No. 1, pp 17–21.*
Burke et al., "Cloning of Large Segments of Exogenous DNA into Yeast by Means of Artificial Chromosome Vectors," *Science,* 236:806–812.
Burmeister and Lehrach, "Long–range restriction map around the Duchenne muscular dystrophy gene," *Nature,* 324:582–585, 1986.
Cangiano et al., "Use of repetitive DNA probes as physical mapping strategy in *Caenorhabditis elegans,*" *Nucleic Acids Research,* 18(17):5077–5081, 1990.
Coulson et al., "Genome linking with yeast artificial chromosomes," *Nature,* 335:184–186, 1988.
Evans and Lewis, "Physical mapping of complex genomes by cosmid multiplex analysis," *Proc. Natl. Acad. Sci. USA,* 86:5030–5034, 1989.
Lawrence et al., "Interphase and Metaphase Resolution of Different Distances Within the Human Dystrophin Gene," *Science,* 249:928–932.
Lichter et al., "Fluorescence in situ hybridization with Alu and L1 polymerase chain reaction probes for rapid characterization of human chromosomes in hybrid cell lines," *Proc. natl. Acad. Sci. USA,* 87:6634–6638, 1990.

(List continued on next page.)

Primary Examiner—Ardin H. Marschel
(74) Attorney, Agent, or Firm—Fulbright & Jaworski L.L.P.

(57) ABSTRACT

The present invention relates to preparation and methods of use of novel extended and super-extended forms of DNA. These forms of DNA are stretched to a substantially linear form up to about 0.6 μm per kilobase pair. The extended DNA may be hybridized with suitably labelled probes and visualized directly. Gene order and distance are rapidly and efficiently determined with a resolution down to 0.4 kb using fluorescent hybridization techniques.

14 Claims, 9 Drawing Sheets

OTHER PUBLICATIONS

Kallioniemi et al., "Comparative Genomic Hybridization for Molecular Cytogenetic Analysis of Solid Tumors," *Science*, 258:818–821, 1992.

Poustka et al., "Construction and use of human chromosome jumping libraries from NotI–digested DNA," *Nature*, 325:353–355, 1987.

Stallings et al., "Physical mapping of human chromosomes by repetitive sequence fingerprinting," *Proc. Natl. Acad. Sci. USA*, 87:6218–6222, 1990.

Trask et al., "the Proximity of DNA Sequences in Interphase Cell Nuclei is Correlated to Genomic Distance and Permits Ordering of Cosmids Spanning 250 Kilobase Pairs," *Genomics*, 5:710–717, 1989.

Weber and May, "Abundant Class of Human DNA Polymorphisms Which Can Be Typed Using the Polymerase Chain Reaction," *Am. J. Hum. Genet.*, 44:388–396, 1989.

Windle et al., "A central role for chromosome breakage in gene amplification, deletion formation, and amplicon integration," *Genes & Development*, 5:160–174, 1991.

Yagle et al., "Genetic and physical map of the von Recklinghausen neurofibromatosis (NF1) region on chromosome 17," *Proc. Natl. Acad. Sci. USA*, 87:7255–7259, 1990.

Botstein et al., "Construction of a Genetic Linkage Map in Man Using Restriction Fragment Length Polymorphisms," *Am. J. Hum. Genet.*, 32:314–331, 1980.

Deininger et al., "Base Sequence Studies of 300 Nucleotide Renatured Repeated Human DNA Clones," *J. Mol. Biol.*, 151:17–23, 1981.

Futreal et al., "BRCA1 Mutations in Primary Breast and Ovarian Carcinomas," *Science*, 266:120–122, 1994.

Glazer et al., "A stable double–stranded DNA–ethidium homodimer complex: Application to picogram fluorescence detection of DNA in agarose gels," *Proc. Natl. Acad. Sci. USA*, 87:3851–3855, 1990.

Greig et al., "Chromosome–specific Alpha Satellite DNA from the Centromere of Human Chromosome 16," *Am. J. Hum. Genet.*, 45:862–872, 1989.

Leach et al., "Physical Mapping of Human Chromosome 17 Using Fragment–Containing Microcell Hybrids," *Genomics*, 5:167–176, 1989.

Lichter et al., "High–Resolution Mapping of Human Chromosome 11 by in Situ Hybridization with Cosmid Clones," *Science*, 247:64–69, 1990.

Litt and Luty, "A Hypervariable Microsatellite Revealed by In Vitro Amplification of a Dinucleotide Repeat within the Cardiac Muscle Actin Gene," *Am. J. Hum. Genet.*, 44:397–401, 1989.

Miki et al., "A Strong Cardidate for the Breast and Ovarian Cancer Susceptibility Gene BRCA1," *Science*, 266:66–71, 1994.

Schwartz and Koval, "Conformational dynamics of individual DNA molecules during gel electrophoresis," *Nature*, 338:520–522, 1989.

Scott et al., "Origin of the Human L1 Elements: Proposed Progenitor Genes Deduced from a Consensus DNA Sequence," *Genomics*, 1:113–125, 1987.

Viskochil et al., "Deletions and a Translocation Interrupt a Cloned Gene at the Neurofibromatosis Type 1 Locus," *Cell*, 62:187–192, 1990.

Wallace et al., "Type 1 Neurofibromatosis Gene: Identification of a Large Transcript Disrupted in Three NF1 Patients," *Science*, 249:181–186, 1990.

Wiegant et al., "High–resolution in situ hybridization using DNA halo preparations," *Human Molecular Genetics*, 1(8):587–591, 1992.

* cited by examiner

METHODS AND COMPOSITIONS FOR EXTENDED AND SUPER-EXTENDED DNA AND HYBRIDIZATION MAPPING

BACKGROUND OF THE INVENTION

This application is a continuation-in-part of application Ser. No. 08/264,802 filed Jun. 23. 1994; now U.S. Pat. No. 5,707,797; which is a continuation-in-part of application Ser. No. 08/002,781 filed Jan. 8, 1993; now abandoned; the entire text and figures of each application being incorporated herein by reference without prejudice and without disclaimer.

FIELD OF THE INVENTION

The invention relates to intact extended and super-extended DNA, methods of producing the extended DNAs and to efficient and rapid mapping of genes and other sequences employing various forms of extended DNA and DNA probes, particularly for visual mapping such as where fluorescent hybridization (comparable to in situ hybridization techniques) is employed. The remarkable sensitivity and resolution of direct visualization detection employing extended DNA permits rapid detailed studies of DNA rearrangements, such as translocations, and select determination of order and distance between DNA segments. Further, the invention concerns methods of controlling DNA extension to tailor to particular needs including long and short range mapping of DNA sequences.

DESCRIPTION OF RELATED ART

A primary goal in developing a genome map is identification of genes and DNA sequences involved in disease states or disorders as well as in normal functions of the cell. The combined use of genetic and physical mapping of the human genome has proven useful in the placement of genes and/or molecular markers in reference to each other and in the cloning and identification of genes of biological and medical significance. This method of identification requires the use of genetic linkage data in a population to connect a disease or biological characteristic with molecular DNA markers. With this information, a physical map can be used to identify a gene of interest by its position in relation to the DNA markers.

The characterization of gene structure and genome organization has been greatly facilitated by the development of a number of physical mapping technologies. Among the first technologies developed were restriction mapping and DNA sequencing, which provide the highest resolution information, but are cumbersome when applied to large regions of DNA.

The development of pulsed-field gel electrophoresis and the use of rare cutting restriction enzymes has opened the door to restriction mapping in the megabase (Mb) size range. For the mapping of still larger regions of DNA, more recent developments of yeast artificial chromosomes (YACs) (Botstein et al., 1980) and radiation hybrid maps (Nakamura et al., 1987) have been useful. However, as the DNA regions to be mapped increase in size, fine structure resolution is generally sacrificed. Other techniques, such as the "finger-printing" of repetitive elements (Litt et al. 1989), have been developed to overcome long range restriction mapping deficiencies.

A more global approach to mapping involves fluorescent in situ hybridization (FISH) to identify the position of probes on metaphase chromosomes (Weber et al. 1989). The use of this technique allows more rapid mapping of DNA probes with approximately 1 Mb resolution. For higher resolution mapping, the FISH technique has been applied to interphase nuclei (Evans et al. 1989). Since the DNA is less condensed in interphase nuclei than in metaphase chromosomes, resolution in the 50–100 kb range can be obtained. However, mapping the distance between two probes in three dimensional nuclei or compressed two dimensional nuclei is complex and requires large data sampling and probability calculations based on a random walk model (Coulson et al. 1988).

Long distance restriction maps of DNA regions have been generated using rare cutting restriction enzymes such as NotI (Poustka et al. 1987; Yagle et al. 1990; Barmeister et al. 1986). NotI linking clones, which encompass a NotI cleavable site, have been used to facilitate NotI mapping by identification of contiguous NotI fragments (Wallace et al. 1989). The use of frequent-cutting enzymes such as HindIII is not practical for mapping megabase-size DNA due to the complexity of the map.

Additional strategies for gathering physical linkage information on a still larger scale include the use of interspecific somatic cell hybrids, in which panels of rodent/human hybrid cell lines that retain various combinations of human chromosomes or parts thereof are used to localize probes to individual chromosomes or chromosomal regions (Ruddle et al. 1971). Radiation-induced hybrids, in which fragments of human chromosomes are retained in a rodent cell background (Goss et al. 1975) have also been employed.

Finally, fluorescent in situ hybridization (FISH) has become popular for determining approximate distances greater than 1 Mb between two or more probes on metaphase chromosomes (Lichter et al. 1990). FISH may also be used to a limited extent to determine the relative order of probes. For example, more closely linked probes along a 250 kb region have been hybridized to uncondensed DNA in interphase nuclei (Trask et al. 1989). While information concerning order may be obtainable with the method, there are some serious shortcomings; a major problem is that DNA in interphase nuclei is three dimensional. Labels that are not closely spaced or which are in reverse order to the observed order may be inaccurately determined because labels appear to be on top of one another, or because a twisted loop is viewed two-dimensionally.

A second shortcoming is the resolution. While improvements have been made, and the predicted resolution with FISH visualization is claimed to be about 10 kb, this range has not been substantiated, although resolution at 21 kbp has been reported (Heng et al. 1992). Higher resolution may be hampered because of the 3-D structure of the DNA, with lack of accessibility leading to poor resolution and difficulty in detection.

There have been reported attempts to reach levels of resolution around 10 kb; in one instance by expelling long 200 μm loops from the nucleus (Wiegant et al. 1992), releasing chromatin fibers (Heng et al. 1992) or creating nuclear "halos" by extending DNA from which histones have been extracted (Lawrence et al. 1992). Although believed possible to extend resolution below 10 kb, there do not appear to be published data demonstrating that such resolution has been achieved.

There is, therefore, a need to develop physical mapping techniques that eliminate the tremendous amount of time and effort needed for restriction mapping and Southern blot hybridization and to increase the resolution limitation associated with FISH methods. New methods would allow microscopic visualization of cosmids or other DNA probes hybridized to an uncondensed fully extended DNA molecule, such as mapping of specific probes with high resolution exceeding 5 kb on YAC DNA. Direct visual mapping of repetitive DNA elements along a DNA strand would provide a significant improvement and alternative to restriction mapping and fingerprinting techniques.

SUMMARY OF THE INVENTION

The present invention addresses one or more of the foregoing or other problems encountered in chromosome mapping, particularly the complexity and inadequate resolution of current techniques. The present invention involves methods of preparing and visualizing DNA strands in linearized, that is, straight-line extended or "super-extended" forms as a means of mapping small or large DNA segments or even gene clusters.

The invention includes a simple, effective method to produce linear, one-dimensional DNA. The method provides extended and super-extended forms of DNA, the latter stretched to a length beyond the calculated "unwound" length of native DNA. By comparison, the DNA from typical "spreads" (Lehninger, 1970) is two-dimensional in the sense of exhibiting two directions in a single plane (including curves and winding). The form of DNA disclosed in the present invention is virtually straight (linear), has no contour and little, if any, randomness. It is thus visualized as extending in only one direction in a single plane. The invention therefore provides a procedure to stretch DNA into novel, linear, one-dimensional forms up to and beyond 0.34 $\mu$m per kilobase pair. The DNA can be used as a target for hybridization of labelled probes to visually observe a high resolution map of probes along a single strand of DNA. Mapping resolutions as high as 1 kb are possible with the extended DNA. Super-extended DNA allows even further increases in resolution to at least 0.4 kb, although the extended form is practical for many applications.

Extended DNA is DNA stretched to a substantially one-dimensional form up to about 0.34 $\mu$m per kilobase pair. Super-extended DNA is an essentially one-dimensional form stretched beyond what is commonly held to be the maximal length of fully extended DNA (0.34 $\mu$m per kilobase pair). The inventors have shown super-extension of DNA up to at least 0.6 $\mu$m per kilobase pair with no evidence of bond disruption. However, the inventors have observed that while the DNA length is stretched, the relative lengths remain generally proportional, i.e., the DNA stretches uniformly at least within limited areas. By varying the lengths of extended or super-extended DNA, rapid and accurate determination of order and distance between DNA segments is possible. Typically, such determinations employ variations of fluorescent in situ hybridization techniques (FISH), although other visualization techniques may be employed.

Stretching of DNA typically involves a gravitational streaming procedure such as allowing an aqueous sample of DNA to run down an appropriate surface; for example, a glass slide. Other procedures for stretching DNA in a linear fashion are possible, such as forced air streaming, the use of a charged field, or mechanical stretching, all of which are well known. In order to fix DNA to the surface over which it is stretched out, any of several fixing compositions may be employed; for example, formaldehyde, paraformaldehyde, glutaraldehyde, acids or alcohols. In a preferred embodiment, a DNA duplex is denatured, but the strands are not physically separated, thus allowing hybridization of probes, if desired, to the anchored strands. Lack of physical separation prevents division of the signal when labelled probes are employed, thus increasing sensitivity.

Accordingly, in one aspect of the practice of the invention, a novel DNA mapping technique employs extended or super-extended DNA hybridized with probes suitably labelled for detection. Standard FISH techniques, for example, permit direct visualization of the extended DNA under the microscope with resolutions as low as 0.4 kb. Other fluorescence visualization methods, or variations thereof, such as scintillography, radiography, chemoluminescence, fluorescence, etc. may also be utilized. Extended or super-extended DNA provides significantly increased resolution and greatly reduced preparation and analysis time.

There are several advantages of the disclosed DNA mapping method. For example, only one hybridization is necessary in order to determine the distance between two probes; thus, a restriction map of a DNA region (e.g., a YAC clone or genomic DNA) is not necessary for determining the distance between two probes. Additionally, very little DNA is required (e.g., 100 molecules (~1 ng) as opposed to $\mu$g quantities). Information is acquired rapidly; for example, in a matter of days for some DNA mapping, rather than the weeks, months or even years required in some cases using standard mapping procedures. Chromosomal DNA can be mapped directly, thus avoiding mapping errors due to possible rearrangements in the clones. Mapping distances as large as 5 Mb between two probes is how feasible (considering size calculated from intact DNA that has been spread using other standard procedures). Using repetitive sequence probes, (e.g., L1, Alpha, or Alu repeats) a repeat map can be generated providing an alternative to the more involved, time consuming, and complex mapping of restriction sites and is a vast improvement over fingerprinting. Yet another advantage of the method is the ability to simultaneously determine the position of a specific sequence probe relative to a repeat map.

It should be mentioned that the length of fully extended, relaxed, duplex DNA is generally accepted as 0.34 $\mu$m per kilobase pair (see, for example, Lehninger, 1970). This value is obtained from X-ray crystallographic data and is considered to be the maximum length of fully extended, double stranded relaxed β-form DNA. Without deliberate stretching, fully relaxed DNA will not normally conform to a straight line. Clearly, however, the accuracy of measurements for straight-line DNA would be superior to measurements of DNA that winds around or overlaps itself. The present invention concerns a method of extending DNA as a straight line beyond its expected maximum of 3.4 $\mu$m per kilobase pair and reaching at least 0.65 $\mu$m per kilobase pair.

Extended or super-extended DNA can be hybridized with labelled probes to accurately determine distances between and order of the corresponding sequences. Direct visualization, such as the observation of multi-colored fluorescent probes under a microscope, provides virtually immediate mapping of DNA segments. Complete mapping is possible in a very short time with this technique; for example, only a few days are required for complete mapping of 15 cosmids covering a 500 kb region. This contrasts with estimates of 6–24 months to construct a similar genomic map by restriction mapping and fingerprinting. If there are gaps between some of the cosmids, additional cloning and mapping may be required by standard mapping. With the present invention, complete mapping is independent of gaps.

In more particular aspects, it has been discovered that stretching of DNA may be varied, much as a rubber band may be stretched to different degrees without breaking. By stretching a DNA thread to the maximum, which herein is understood to mean close to the point where covalent bonds are broken, short range distances along a gene or DNA sequence may be determined. Lesser degrees of stretching, e.g., linearization to a kilobase pair distance of about 0.34 µm) are more suitable for longer range mapping.

As mentioned, the disclosed method of producing super-extended DNA involves stretching and then fixing DNA. One will generally employ cellular DNA, although DNA isolated from any source such as genomic DNA or cloned DNA may also be used.

Where cells are employed as the DNA source, the DNA is obtained by first disrupting the cell prior to stretching the DNA. Several methods of releasing the DNA from the cell may be employed including mechanical disruption, sonication, enzymatic degradation, hypotonic bursting, heat shock or cold shock. A convenient and preferred method is to treat the cellular DNA with a detergent. The detergent may be anionic, cationic or neutral and is preferably sodium dodecyl sulfate. The effect of the detergent is to dissolve the lipid material of the cell wall, denature and release proteins complexed to DNA thereby releasing the DNA.

The amount of sample DNA that is analyzed depends on the amount of data desired. For example, in order to map regions of DNA where hybridized DNA probes are observed under the microscope, very small amounts of DNA are required. Thus, a typical amount for cellular DNA samples comprises about 100 to 5,000 cells, i.e., 1–5 ng of cellular DNA.

In order to effectively stretch the DNA to an extended or super-extended form the DNA will be suspended in fluid. When cells are used as a source of a DNA sample this is generally no problem and intracellular disrupted suspensions may be used with or without further addition of fluid to the sample. Preferable fluids for suspension are basically aqueous, and can range from unbuffered to buffered solutions with phosphate, Tris or other salts. For highly concentrated samples of DNA or freeze dried samples, of course, a fluid should be added to create a suspension in order to affectively stretch out the DNA using the disclosed methods. While it is generally preferable to use aqueous solutions, other fluids such as alcohols and other organic solvents may be mixed with the aqueous media, preferably in relatively low amounts, e.g., 10% alcohol/water. Such mixtures would be expected to have the effect of altering the rate and amount of extension and may be tailored for particularly desired types of extension of the DNA molecule.

The disclosed extended or super-extended DNA is stretched by streaming the DNA over a supporting surface. Methods of DNA streaming include gravitational streaming, forced air or fluid streaming and stretching induced by charged electric fields, although other related methods such as mechanical stretching of DNA may also be employed. The gravitational streaming method involves tilting the supporting surface at an angle which will efficiently extend the DNA. Generally, the angle of tilt will be between about 20 to about 90 degrees from horizontal. The tilt angle employed will, of course, depend also on the surface employed for the support. Differences in surface material and surface tension of the DNA solution may affect the rate of streaming and the ultimate extension of the DNA molecule.

The support surface over which the DNA is gravitationally streamed should be relatively smooth and inert as to its reaction with the DNA. Glass or plastic are particularly preferred surfaces because these materials are used for microscope slides and several of the methods employing super-extended DNA utilize microscopic visualization. Other suitable support materials include ceramics, metal surfaces, cellophane or nitrocellulose and chemically coated surfaces.

Subsequent to stretching by gravitational streaming over a supporting surface the DNA is fixed to the surface. Fixing is generally by a chemical treatment although other means of attachment to the surface may be employed; for example, by UV crosslinking. Cellular DNA, after release from the cell, is surrounded by proteins. The fixative will therefore act to anchor the DNA to the proteins and the proteins will be anchored to the surface. Direct anchoring of DNA to the surface is also possible. In the case of purified DNA without protein, the addition of protein may facilitate the DNA anchoring process. Numerous commonly available fixatives may be employed, such as methanol/acetic acid mixtures, formaldehydes, glutaraldehyde or heat. Alcohol and common mineral or organic acids are effective and inexpensive fixatives. Methanol and acetic acid mixtures are particularly preferred for fixing cellular DNA to a solid surface.

In preferred practice, extended or super-extended DNA is in duplex form and is fixed to the matrix over which it has been stretched. The fixing conditions employed are such that the DNA duplexes are denatured but do not appear to separate. Denaturation allows hybridization of probes, yet the two strands are anchored sufficiently to keep them from appearing as two strands. The resulting signal, typically fluorescence labels, is at least twice as bright as probe hybridized to a single isolated strand.

In one aspect of the invention, a method of DNA mapping is disclosed. The mapping method generally includes the steps of obtaining a DNA sample, forming extended or super-extended DNA, hybridizing the DNA with a suitable probe and then determining the position of the probe on extended DNA. By employing extended or super-extended DNA and labelling with a probe that is easily visualized, relative probe position and order are readily and quickly determined. The high resolution obtained is possible because the super-extended DNA is substantially linear with distance greater than 0.34 µm per kilobase pair. The distance per kilobase pair may be extended as far as 0.65 µm. Since the extension results in a substantially linear form, that is, a flat single-dimension rather than a 3-dimensional matrix the straight line form of the DNA allows easy measurement of appropriate labels that show position and order. DNA probes may be labelled with direct or indirect forms of fluorescent labels, radiolabels, luminescent or calorimetric labels. Labels may include conjugates to nucleotides such as biotin, DNP, digoxin or the like.

Two aspects of the sensitivity of the disclosed method are quite surprising. These appear to be related to the disclosed procedure for stretching and fixing DNA. Sensitivity of detection of a DNA size in the range of 5 kb is readily obtained and sensitivity down to 0.4 kb has been determined. The high sensitivity is greater by at least an order of magnitude than standard FISH can attain and appears due to the DNA being extended rather than compressed in the nucleus. For hybridized target DNA that is compacted in a small space, there is little room for binding of proteins such as the avidin used in the detection system. While the bound probe in a compressed nucleus may have a greater capacity to bind the detection proteins, steric hindrance appears to effectively hinder binding. On the other hand, the hybridized extended DNA has protein binding sites far from each other with little contact; thus, there is less or negligible steric hindrance and a greater capacity to bind the labelled proteins.

The second aspect of sensitivity obtained with the present invention relates to the small number of molecules required to generate mapping information. Theoretically, a single cell may be lysed and its DNA stretched and analyzed. This is in stark contrast with the more than one million cells required for a single Southern blot analysis.

Visualization directly under the microscope to determine relative order and distance between DNA segments will be referred to herein as DIRVISH DNA mapping, which is understood to mean direct visual hybridization DNA mapping. Measurement of physical distances that represent map distances has been referred to previously.

Labelled probes may be hybridized to cellular DNA using methods well known to those of skill in the art. In preferred embodiments, detection of labelled probes is by direct visualization; for example, by direct visualization of fluorescent probes. Various probes may be differentially labelled, for example, with one, two, three, or more different fluorescent probes that are visualized under the microscope as different colors. Visualization need not be by fluorescent microscopy, however, and other methods, such as light microscopy or scintillography could be used for detection.

It is contemplated that DNA desired for mapping will most usually be cellular DNA. Cellular DNA will be duplexed DNA and is preferably treated with a chromatin-disassociating agent prior to extension. In some cases it may be beneficial to denature the DNA duplexes prior to extension.

In genome mapping, DIRVISH DNA mapping can be used to rapidly map the position and order of either restriction fragments, cosmids or YACs. With the development of 12 color fluorescent probe labelling, it is possible to map 12 probes, such as restriction fragments, simultaneously.

A common strategy to identify a gene responsible for a genetic disease is to use genome mapping to narrow the region of interest to ~1 Mb. The 1 Mb region is then analyzed by a variety of restriction mappings and Southern blot hybridizations using several different probes to identify potential disease causing deletions, inversions or insertions that may allow one to pinpoint the location of the disease gene. DIRVISH DNA mapping can map such a region in a normal cell within one week, and will rapidly detect and pinpoint alterations in the gene from a small number of patient's cells as part of a routine screen. An example of this is the NF-1 gene of neurofibromatosis patients which can be identified by three different deletions of 190 kb, 40 kb and 11 kb, all of which are easily mapped by DIRVISH DNA mapping.

A rapid and simple screen of rearrangements in known disease associated genes is possible using DIRVISH DNA mapping using a very small cell sampling. Detection of rearrangements can be diagnostic and prognostic; for example, the detection of deletions in the NF-1 gene in the diagnosis of patients with neurofibromatosis type 1, or the detection of abl-bcr rearrangements in patients as a means of diagnosis and prognosis based on pinpointing the breaksite junction. The detection of rearrangements in the Duchenne's muscular dystropy gene would serve as a diagnosis of that disorder.

In further aspects, the present invention concerns a kit for mapping DNA. The kit includes an apparatus for extending or preparing super-extended DNA and also contains any of numerous probes suitable for hybridization with segments of a DNA of interest. The probes may be labelled with a variety of labels, for example, fluorescein, biotin or the like.

An apparatus such as that shown in FIG. 1 for preparing extended or super-extended DNA will include a tiltable surface preferably adjustable to an angle between 0 to 90 degrees from horizontal. The angle may be adjusted mechanically by hand; for example, by a step-adjustable lock mechanism or alternatively adjustable through electronic means such as chip powered batteries or externally supplied power. The apparatus may include mechanisms for automatically varying the tilt angle over a specified period of time. The apparatus may also provide for handling of several samples simultaneously with the same or different tilting angles.

Yet another aspect of the invention includes novel extended forms of DNA produced by gravitationally stretching DNA (see FIG. 2A). Such extended DNAs are unique forms of DNA with several differences in properties, compared to the three-dimensional, relatively compact forms of DNA normally encountered in the cell (see FIG. 2B). The extended or stretched forms of DNA have an interkilobase pair distance equal to or less than 0.34 $\mu$m. Super-extended DNA has an interkilobase pair distance of greater than 0.34 $\mu$m per kilobase pair and up to or beyond 0.65 $\mu$m.

The invention therefore provides a much improved mapping technique with many practical and clinical applications. Clinically, the method better pinpoints translocation breakpoints using small sample size, in some cases even a single cell. Structural changes in genes may be detected in small or heterogenous samples. Examples include the analysis of amnionic fluid or p53 gene deletions in tumor samples where cosmid probes cover a 400 kb region, alternating colors with one end labelled with another probe, or mapping regions of replication which can provide a physical reference point and map for detecting position of origins.

Additional applications include quick mapping of restriction fragments in the genome or cosmid, mapping orientation of cosmid to any other probe site, mapping one cosmid to another cosmid (overlap or gap), mapping restriction fragments in YACs, YAC to YAC (overlap or gap), or orientation of YAC to another probe site, mapping sites of exons >0.4 kb in a gene using cDNA probes, mapping sites of PCR products such as inter-alu PCR, producing unique patterns for specific regions, mapping unique patterns for specific regions, mapping repeats such as Alu or Line or Alpha in specific regions, producing unique patterns as a map for ubiquitous repeats (Alu or Line) mapping on YACs directly from yeast cells or genome fragments from somatic or radiation hybrids, mapping unique probes from NotI linking or jumping library or related systems, detecting rearrangements; for example, inversions, deletions, etc. in cosmids, YAC clones by comparison to genomic DNA or mapping rearrangements in genes for diagnostic significance.

BRIEF DESCRIPTION OF THE FIGURES

FIG. 2.

FIG. 14 shows two scans through DIRVISH strings from the probing with a cosmid showing that the patterns were similar.

DETAILED DESCRIPTION OF PREFERRED EMBODIMENTS

Figure 1:
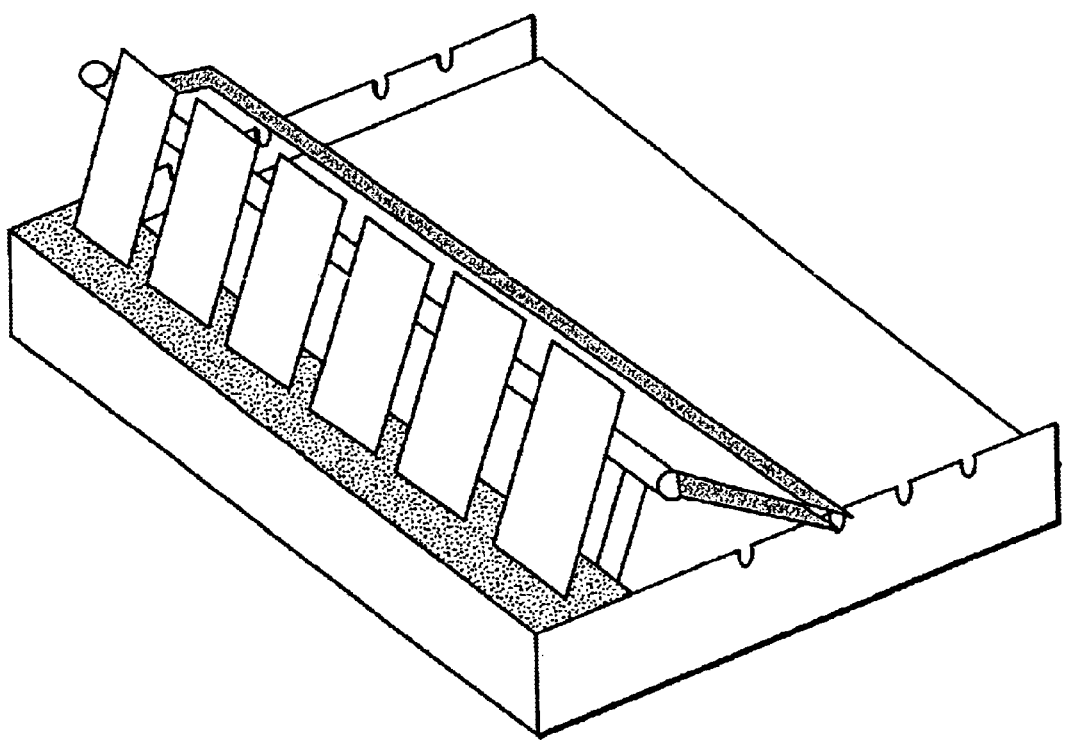
FIG. 1 is a schematic representation of an example of a variable-tilt holder for a matrix employed to gravitationally stretch DNA across a supporting surface.

In general, the disclosed method offers advantages over other systems such as restriction mapping, FISH interphase nuclear mapping, FISH metaphase mapping, fingerprinting with repeats and halo-extended DNA. The advantages over these methods including those employing histone-extracted unwound DNA are several, including:

DNA is stretched in a straight line, thus eliminating measurement errors

DNA is stretched beyond its known limits, unlike spread DNA

DNA is not manipulated, so it remains intact over large distances

Preparation is simple, no histone extraction, in contrast with spreading techniques DNA is found only in distinct easily located streams as opposed to spreading which places DNA over a wider area Only a few cells are required Resolution sensitivity is improved The potential for using fluorescent hybridization on extended or super-extended DNA to map long stretches of a gene has been demonstrated. Feasibility has been shown in studies in which chromosomal DNA molecules as large as 5 Mb in length, and in one case 60 Mb in length, have been spread intact on a surface. The ability to visualize microscopically a strand of DNA indirectly or by direct fluorescence makes quantitative measurements of actual distance and conversion to kb practical and simple. The use of multiple probes and sensitive fluorescent marker detection permits simultaneous probe mapping. The method disclosed herein is an improved and expedited physical gene mapping technique.

The disclosed method of gene mapping is a significant improvement over other methods. Typically with the new method gene mapping may require only two days, the mapping data are direct, visual, intuitive and require little deduction or inference. The map of the DNA is genomic rather than clonal (i.e., there is no chance of clonal rearrangement), resolution is as low as 0.4 kb, mapping is short (~5 kb) or long range (500 kb or greater) on the same DNA preparation, and the orientation of linked clones to each other and the distance between them may be determined without identification of the intervening DNA. Unlike any other high resolution mapping procedure, a complete DIRVISH DNA map is generated regardless of the gaps.

A variety of forms of molecular DNA markers or polymorphisms have been exploited for linking genetic and physical maps, including restriction fragment length polymorphisms (RFLP), which result from a change in a restriction endonuclease recognition site (Botstein et al., 1980), and variable number tandem repeats (VNTR) (Nakamura et al., 1987). More recently, PCR probes have been used to detect polymorphisms in the lengths of simple repeats, such as $(CA)_n$ (Litt et al., 1989; Weber et al., 1989).

Generating physical maps of such DNA markers requires probes for regions derived from cloned genomic DNA. The cloning of genomic DNA (up to 47 kb) into cosmids is one of many approaches for deriving probes for various types of mapping such as detailed restriction mapping, and ultimately, for DNA sequencing. In addition, cosmid clones can be used for isolating flanking cosmid clones, in either direction by "chromosome walking" (Evans et al., 1989) to form a "contig." Chromosome walking using cosmids, however, only allows steps of at most 40 kb to be taken.

Chromosome jumping was devised to permit the cloning of DNA from both ends of a NotI fragment (separated by many hundreds of kb) without chromosome walking (Poustka et al. 1987). However, the development of yeast artificial chromosomes (YACs) for cloning genomic DNA as large as 1 Mb (Burke et al. 1987) has circumvented this approach, since chromosome jumping does not identify DNA between the jump.

The use of YACs was a significant advance over large scale restriction mapping, determining physical linkage between probes, and chromosome walking. However, cosmid clones are still used for many types of probes and for sequencing, since there are not adequate means for purifying YAC DNA in substantial quantities. The combined use of cosmids and YACs has provided to date one of the more effective approaches to genome mapping (Coulson et al., 1988).

There are, however, many drawbacks to this combined technique in genome mapping. While it is a simple matter to determine whether a particular cosmid (or cosmids) contains DNA represented within a YAC or a chromosomal region, it is necessary to construct a restriction map of the YAC to determine the location of the cosmid sequences within the YAC or to determine the relative positions of multiple cosmids. On a larger scale, the relative positions of multiple YACs is also unnecessary. Stallings et al. (1990), have developed a fingerprinting strategy using repetitive sequence hybridization to restriction fragments for determining overlap of two cosmids or YACs (Cangiano et al. 1990). However, if the clones do not overlap, a more involved mapping strategy is needed.

In contrast, the disclosed method of gene mapping is rapid and efficient. The use of computer imaging analysis even further increases speed and analysis time. For computer analysis, digitalization of the images is used. Several options may be employed. The most direct method is to record the image through the microscope directly with a color CCD camera. A high resolution image is obtained when using a 0.8–5× zoom lens coupler and a 100× objective with the CCD camera.

Alternatively, images may be stored on Kodak color slide film, a high resolution, color-based system. The slides are then digitized by either a CCD camera or a slide scanner. A CCD camera and imaging system made by American Innovision and the 0.8–5× zoom lens coupler constitute an efficient and fast means of image acquisition.

Images for a set of slides may be analyzed using the American Innovision image analysis system in conjunction with American Innovision software plus custom software. Image analysis includes determining contour length of DNA strands, the contour length of hybridization signals along the DNA strands, the coordinates and the distances between the edges and center of each fluorescent marker, and a scan of signal intensity along the length of the DNA. The measurements from numerous images are compiled to make a consensus map. As few as ten images are sufficient to demonstrate reproducibility in the map.

The following examples are included to demonstrate with more particularity the techniques and methodology employed by the present inventor to utilize the novel extended DNA and mapping procedures disclosed herein, in particular the utility in mapping of gene order and distance. It should be appreciated that as such these examples are exemplary only and that a variety of possible ways of achieving the same end will be apparent to those of skill in the art in light of the following disclosure. For example, the methods should be amenable for mapping of extremely large genes or DNA regions in a relatively short period of time. All such modifications are intended to be within the spirit and scope of the invention.

EXAMPLE 1

Detecting and Visualizing a Molecule of Super-Extended DNA

To map a region of DNA with this strategy, a fully extended strand of DNA must be visualized. Such visualization may be accomplished using DAPI staining. Visualization of blue fluorescence through a fluorescence microscope is used to follow the migration of individual DNA strands through agarose. This mapping strategy is based on the principle that a small region of DNA (e.g., 5 kb) when extended to the theoretical maximum for relaxed duplex DNA covers a distance visible by the light microscope. Based on the dimension of 0.34 nm per kilobase pair for β form DNA, a 5 kb fragment would extend 1.7 µm; a 40 kb cosmid would extend 13.6 µm, and a 500 kb YAC would extend 170 µm. Standard or modified FISH techniques provide the means of detecting the extended DNA strands through a fluorescence microscope.

Figure 2A:
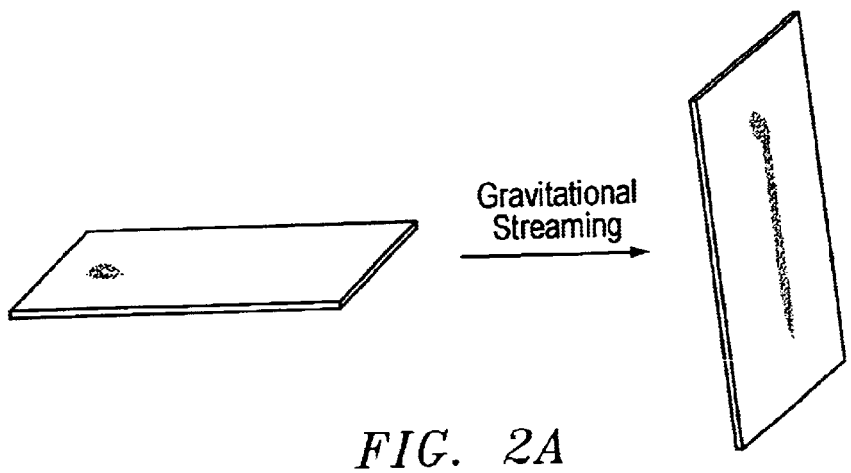
FIG. 2A is a diagram showing the gravitational streaming.
Figure 2B:
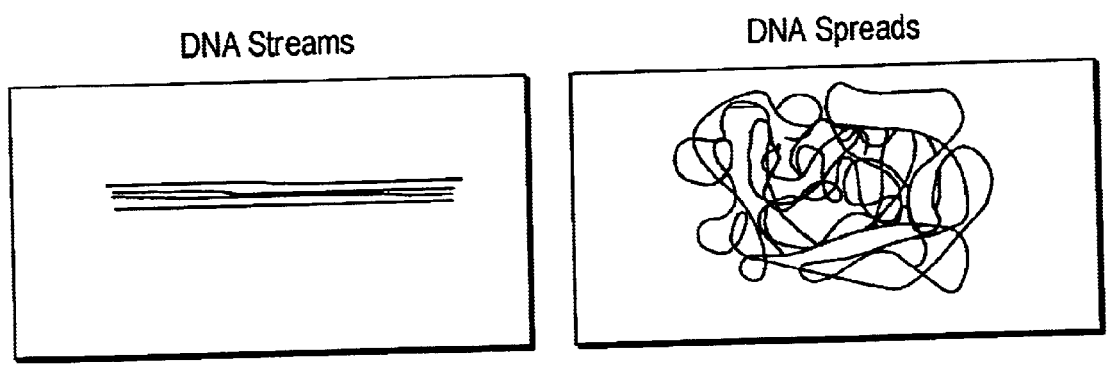
FIG. 2B is a diagram showing a comparison of DNA streams to DNA spreads.

The extension of duplex DNA strands was accomplished by placing individual cells (100–5000) in two µl of PBS on one end of a glass slide and letting the drop dry. Immediately after drying, 5 µl of 0.5% SDS/50 mM EDTA/200 mM Tris, pH 7.4 solution was placed on the dried spot to dissolve the cells and release the DNA. After 5 minutes of dissolving, the slide was tilted to allow the drop of SDS and DNA to run down the slide. This resulted in a DNA stream extending down the slide (FIG. 2A). The DNA stream was allowed to air dry and was then fixed to the slide by flooding the slide with a 75% methanol/25% acetic acid fixative. The DNA was fixed to the slide for 1–5 minutes, the excess fixative drained, and the slide air-dried. Slides were used immediately or stored in slide boxes under $N_2$ with drierite, at −20° C. until used for hybridization.

The effect of the angle on the DNA stretching process had an insignificant effect on maps <40 kb. The less turbulent streaming that occurs on a slide with a low angle (e.g., 20°) appears to help preserve the long stretches of DNA (e.g., >800 kb). Six different angles, selected between 20°–90°, had no apparent effect on the DNA extension of cosmid encoded sequences in the genome. In examining the degree of extension relative to distance from the point of application of the sample on the glass slide, greater extension occurred for longer distances over which the sample had flowed. Thus for long range maps, less extended DNA near the origin is preferred so that the region fits into the field of view.

DNA probes were prepared by nick translation with 30 µM of each of the four nucleotide triphosphates and 100 µm of either biotin—dUTP (BMB) or digoxigenin-dUTP (BMB) or both. The single strand size range for the probes was 100–1500 bp with 500–1000 bp being optimum with respect to high signal strength and low background. The labelled DNA was purified from unincorporated nucleotides by a Sephadex G50 spin column for biotin labelled DNA and a BioRad P60 chromatography column for the digoxigenin labelled DNA. Sephadex appeared to bind digoxigenin and is thus not suitable for purification. The enzymes were denatured with 0.05% SDS and a 5 minute 37° C. incubation prior to column purification. Nucleotide incorporation was monitored by incorporation of tracer $^{32}P\alpha dCTP$. Only probes with greater than 10% incorporation were used.

Hybridization of the probes to the DNA streams followed the general procedures described by Pinkel et al, (1986). Slides were treated with RNAse (100 µg/ml for 30 minutes at 37° C. Slides were then placed in 70% formamide, 2×SSC at 70° C. for 3 minutes to denature the strands followed by immersion in cold 70% ethanol (2 minutes) 90% ethanol (2 minutes), 100% ethanol (2 minutes), then dried. The 20 ng of probe was mixed with 10 µg of sheared hamster-DNA (100–500 bases single strand size range) and dried. The probe was resuspended in 2 µl of $H_2O$ and mixed with 8 µl of hybridization mix (69% formamide, 1.25×SSC, 12.5% dextran sulfate). The probe was denatured at 70° C. for 5 minutes then placed on ice. The 10 µl probe solution was applied to an area of the slide with the DNA stream, covered with a cover slip and sealed with rubber cement. The slide was incubated at 37° C. for approximately 18 hours. The cover slip was removed and the slide washed twice in 50% formamide, 2×SSC for 3 minutes followed by two washes in 2×SSC, all at 45° C.

The detection of biotin was performed according to standard procedures. Avidin block (1% BSA/4×SSC, 5% non-fat dry milk, Carnation) was applied to the slide and incubated at room temperature for 10 minutes. Avidin DN (Vector Labs), 5 µg/ml in 1% BSA/4×SSC was applied to the slide and incubated at room temperature for 20 minutes. The slide was washed for 2 minutes at room temperature with each of the following: 4×SSC, then 0.1% Triton X100/4× SSC, then 4×SSC, then 0.5% NP40/0.1M $NaPO_4$ at pH 8.0. Amplification was performed by applying 4% goat serum in 0.5% NP40/0.1M phosphate buffer at pH 8.0) to the slide and incubating 10 minutes at room temperature, followed by goat biotinylated anti-avidin 5 µg/ml in 4% goat serum 0.5% NP40/0.1M phosphate buffer at pH 8.0 incubated for 20 minutes at room temperature. The slide was washed as described for the avidin procedure. Avidin block was again applied and incubated as described above. Fluorescein-avidin DN or Texas red avidin-DN (Vector Labs), 5 µg/ml in 1% BSA/4×SSC was applied to the slide and incubated for 20 minutes at room temperature. The slide was washed as described above. For immediate viewing, an anti-fade solution VectaShield® (Vector Labs) was applied to the slide and covered by a cover slips.

The detection of digoxigenin was performed by a modified standard procedure analogous to the avidin detection. A pre-Ab block, 4% goat serum/0.5% NP40/0.1M phosphate buffer at pH 8.0 was applied to the slide for 10 minutes at room temperature. Mouse anti-digoxigenin Ab (BMB), at 10 µg/ml in pre-Ab block, was applied to the slide and incubated for 20 minutes at room temperature. The slide was washed as described for avidin detection. After a 10 minute pre-Ab block, digoxigenylated anti-mouse Ig-F(ab')$_2$ fragment, 10 µg/ml in Ab block, was applied and incubated for 20 minutes at room temperature. The slide was washed as described. After a 10 minute pre-Ab block, fluorescein or rhodamine labelled anti-digoxigenin Fab fragment was applied to the slide (25 µg/ml in Ab block) and incubated for 20 minutes at room temperature. The slide was washed as described and antifade applied.

The fluorescence microscopy used a triple band-pass filter (Omega Optical) which allows the simultaneous visualization of fluorescence by DAPI, fluorescein and Texas red or rhodamine. A Nikon Labaphot 2A and a Planapo 100×1.4 was used. Film photography was performed using Ektachroine ASA 400 slide film. CCD photography was accomplished using the American Innovision V150 color imaging system. CCD photography typically required only 0.5 second exposure versus a 20-second exposure for film photography.

EXAMPLE 2

This example provides a more detailed comparison between DIRVISH DNA mapping and restriction mapping. Positions of three restriction fragments were mapped from c400-30 with respect to each other.

Comparison of DIRVISH with Restriction Mapping

Using a 4.8 kb fragment as a reference, the position of two other restriction fragments (6.4 kb and 7.3 kb) known to be derived from opposite ends of the cosmid insert were mapped. DIRVISH DNA maps, determined by two-fragment combination hybridizations (4.8 kb plus 7.3 kb, and 4.8 kb plus 6.4 kb), were produced and compared to the known restriction map, see FIG. 3 and FIG. 4. Though the restriction and DIRVISH DNA maps are generally in close agreement, the DIRVISH DNA consensus maps tend to portray fragments as shorter than actual size. This is likely due to incomplete hybridization of the probes at the ends of the target regions and is overcome by using more probe. Remarkably, the DNA in these two DIRVISH DNA maps is stretched to approximately twice the theoretical maximum of 0.34 µm, i.e., >0.6 µm. The resolution of this type of map is estimated at 0.4 kb, which is the distance of mapped overlap between the 4.8 kb and 7.3 kb fragment shown as a yellow or orange region.

Figure 3:
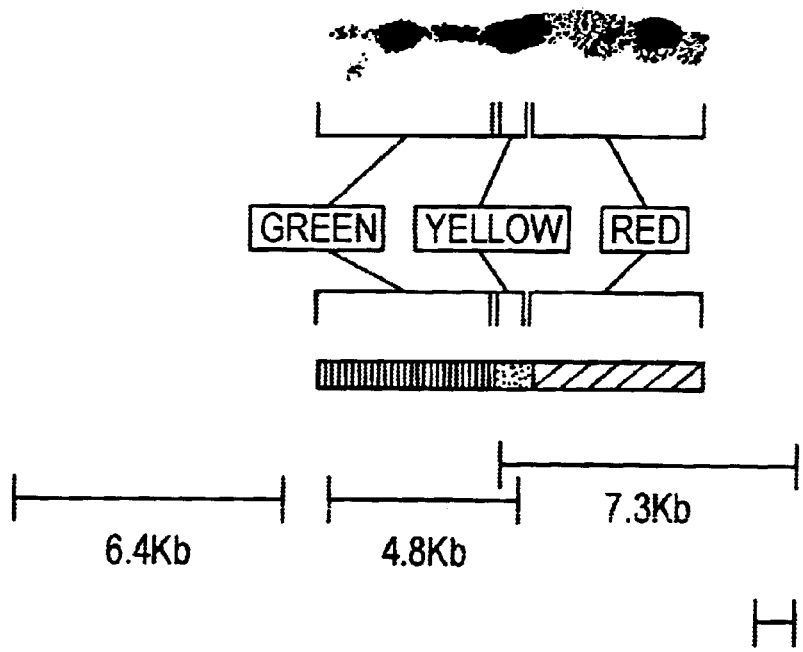
FIG. 3 is a diagram showing a DIRVISH DNA map of two restriction fragments, a 4.8 kb and a 7.3 kb fragment, respectively labelled in green and red.
Figure 4:
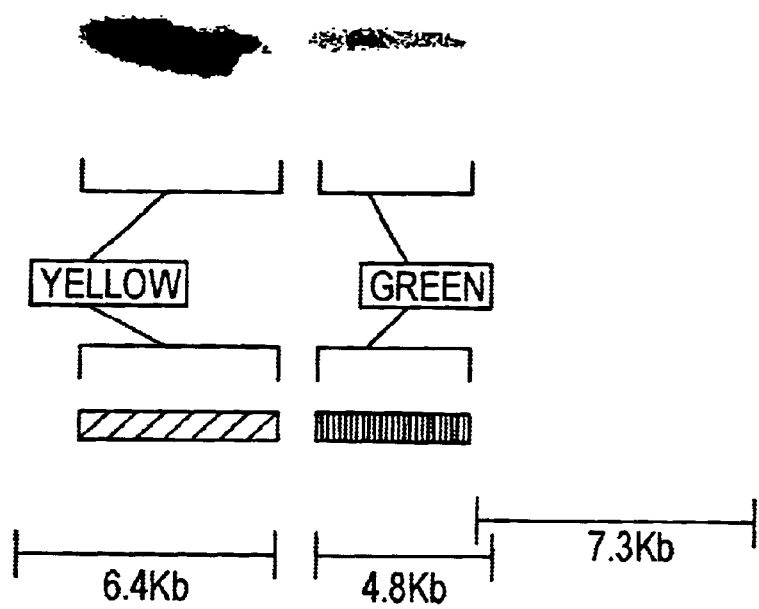
FIG. 4 is a diagram showing a DIRVISH DNA map of two restriction fragments, a 6.4 kb and 4.8 kb fragment, respectively labelled in yellow and green.
Figure 5:
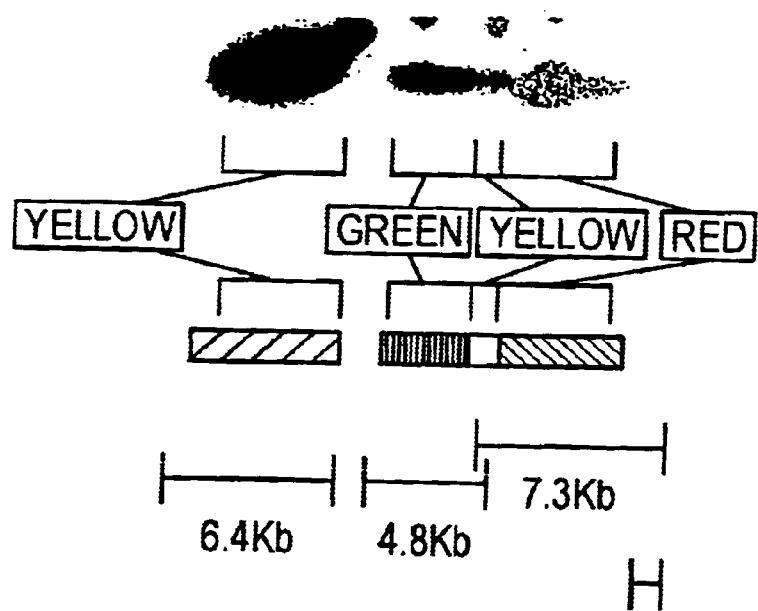
FIG. 5 is a DIRVISH DNA map of three restriction fragments from a cosmid and a schematic representation diagram of the mapping results compared with a restriction map of the three fragments.

The DIRVISH DNA maps of the two restriction fragments are shown in FIG. 3 and FIG. 4 as they correlate with the restriction map. FIG. 3 demonstrates the highest resolution corresponding to 0.4 kb. A three-probe hybridization utilizing three colors (red, green and yellow) was employed to demonstrate their relative positions. The yellow fluorescence was attained by labelling one of the probes simultaneously with both biotin and digoxigenin. The results, shown in FIG. 5, indicate that the position of the three fragments determined by the DIRVISH DNA map are completely consistent with the restriction map.

Figure 6:
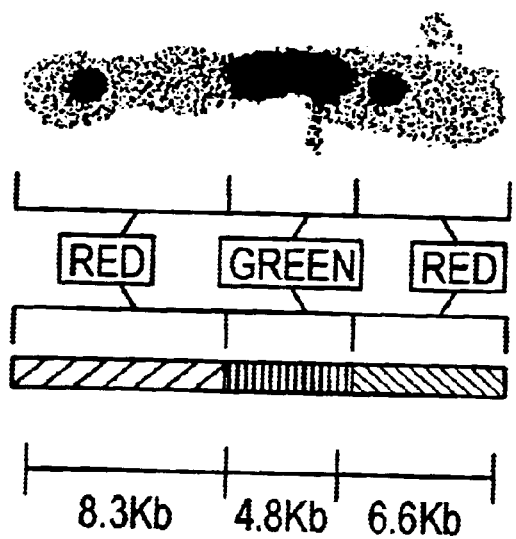
FIG. 6 is a DIRVISH DNA map of a restriction fragment's position in cosmid sequences and a schematic representation diagram of the mapping results compared to a restriction map of the cosmid.

FIG. 6 shows a DIRVISH DNA map of the 4.8 kb restriction fragment and the cosmid from which it was derived.

Figure 7:
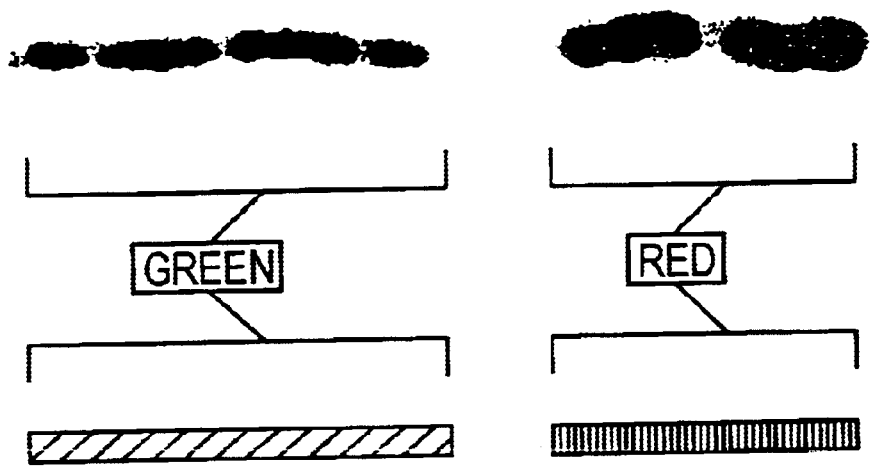
FIG. 7 is a DIRVISH map of cosmids C400-30 and C400-13 with a schematic representation diagram of the mapping data.

To demonstrate the usefulness of DIRVISH DNA mapping over longer ranges of DNA, the position of cosmid c400-30 with respect to cosmid c400-13 (isolated from the 5' end the hamster DHFR gene) was determined. Although the two cosmids are known to be closely linked, they did not overlap, as indicated by Southern blot hybridization. A DIRVISH DNA map using the two cosmids is shown in FIG. 7. This demonstrated that the two cosmids are linked but not overlapping. A distance of ~6 kb between the two cosmids was determined.

Figure 8:
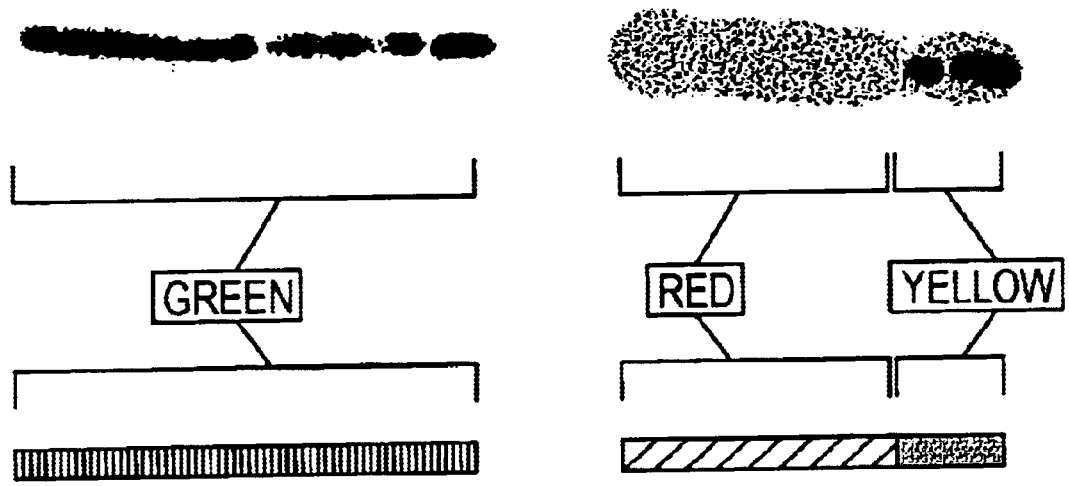
FIG. 8 is a diagram showing a DIRVISH DNA map of two cosmids separated by ~6 kb. One cosmid is labelled in green and the other labelled in red with the orientation fragment labelled in yellow.

Chromosome walking has been used to identify of region between two known probes. This often involves random walking since the relative orientation of the cosmids may be unknown. DIRVISH DNA mapping is particularly useful for determining the relative orientation of two cosmids, thus eliminating the need for random walking. A DNA fragment (labelled with biotin and digoxigenin) from one end of the c400-30 insert was hybridized in conjunction with c400-30 and c400-13. The yellow signal from the asymmetric probe was clearly distal to c400-13 and thus shown to be useful as a probe for chromosome walking away from c400-13 (FIG. 8).

Determining the relative orientation and distance between two such cosmids by restriction mapping procedures would normally require the identification of a restriction fragment or fragments that overlap the two cosmid sequences or the isolation and mapping of overlapping cosmid clones. Neither alternative allows mapping the distance at the high resolution shown with DIRVISH mapping. DIRVISH DNA mapping provides a significant advantage over standard restriction mapping and cloning methods since it required only two days and generated an answer directly with one hybridization. It also provided a fairly precise measurement of the distance between two probes and unambiguous orientation data without having to characterize the intervening DNA.

To further demonstrate the application of DIRVISH DNA mapping over longer distances and the application to studying biologically significant rearrangements, the structure of an amplified gene locus was determined. Determining the structure of amplified genes has proven valuable in elucidating the mechanism of their formation. However, using standard cloning and restriction mapping techniques, this characterization is usually a difficult and time-consuming process. This is particularly true because of the repetitive and complex nature of amplification arrays.

Figure 9:
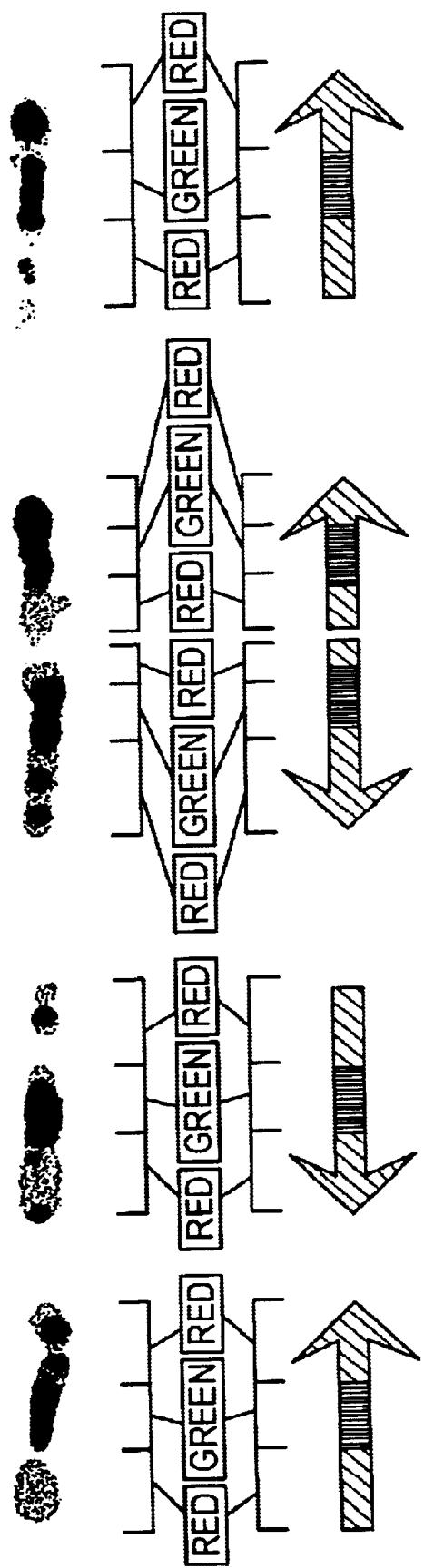
FIG. 9 shows a DIRVISH DNA map of an abnormal DNA with multiple cosmid C400-30 and an internal restriction fragment in red and green respectively. Also shown is a schematic representation diagram of the mapping data. Each array is mapped as a ~50 kb unit.

A DIRVISH DNA map of an amplified DHFR locus in a hamster cell line was generated. These cells have previously been shown by FISH analysis of metaphase chromosomes to contain approximately 8 DHFR genes clustered at the end of one chromosome (Windle et al., 1991). The spacing between the amplified DNA units and the arrangement of DHFR genes could not be determined by standard FISH analysis. FIG. 9 shows the DIRVISH DNA map of cosmid c400-30 and the 4.8 kb fragment-sequences within the amplified DHFR locus. In this image there is an array of 5 units of red and green c400-30 and 4.8 kb fragment signals. There appears to be rearrangement of sequences between one end of c400-30 and the 4.8 kb fragment, as seen by two yellow signals amidst the red signal of c400-30 in addition to that of the 4.8 kb fragment (see the first amplicon on the left). The spacing between each signal cluster is variable, ranging from 1 kb to 50 kb. The size of the largest amplicon is calculated to be ~46 kb. Analysis of this DIRVISH DNA map suggested a structure shown in graphic representation in FIG. 9. The configuration of the array indicated by this and other DIRVISH DNA map data is that of a combination of direct and inverted repeats. There was considerable diversity in the apparent amplification structure as judged by the diversity in the DIRVISH DNA maps of individual structures. This diversity in structure and the subtle rearrangements observed would normally escape detection and characterization using standard restriction mapping and cloning.

The mapping of another amplified DHFR structure in hamster cells was determined by restriction mapping of cosmid contigs. This showed amplified units of ~270 kb with a mix of inverted and direct repeated units. The DIRVISH DNA map provided similar information but required only 2 days to obtain data that was much easier to interpret.

EXAMPLE 3

Application of DIRVISH DNA Mapping to a YAC Clone of Human DNA

This example illustrates hybridization of a 500 kb YAC probe to extended human DNA and use of DIRVISH DNA mapping to determine deletions in the YAC.

Figure 10:
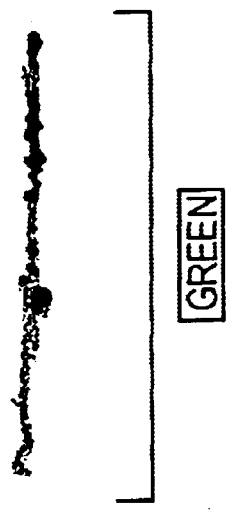
FIG. 10 is a DIRVISH DNA map of a 500 kb YAC encoded region.

A 500 kb YAC containing DNA from the NF1 region of human chromosome 17 was obtained from Dr. Peter O'Connell, University of Texas Health Science Center at San Antonio, Dept of Pathology, Texas (Viskochil et al. 1990; Wallace et al. 1990). The YAC probe was labelled with biotin and visualized with fluorescein labelling. The DIRVISH DNA map appears as a contiguous signal covering the length of the YAC (FIG. 10). This indicated that there were no deletions, which if present would appear as a gap in the signals.

EXAMPLE 4

The following example is provided to illustrate a related use of the disclosed novel mapping method.

DIRVISH DNA Mapping Using Radiation Hybrids

Mapping the distance between two probes on a YAC using the DIRVISH technique depends on obtaining a YAC clone encompassing the two probes. Since many probes of interest may not have been cloned into YACs or may be separated by too great a distance to be encompassed by a single YAC, the DIRVISH technique is ideally adapted for mapping the relative positions of probes directly on genomic DNA. One method is to use radiation-hybrid cell lines, such as 7AD-4 (available from Dr. Robin Leach, University of Texas Health Science Center at San Antonio, Tex.) in which less than $10^7$ bp of human chromosome 17 DNA is embedded in a hamster chromosome (Leach et al. 1989). This region of DNA encompasses the NF1 locus and the two NF1-linked cosmid clones, 1F10 and 7D5.

The strategy is to make extended DNA streams from these cells and label the entire 0.10 Mb length with a probe specific for this region, such as an inter-alu PCR probe. In conjunction with the inter-alu PCR probe, cosmids or YAC probes (labelled with digoxigen) could be hybridized to determine their positions along this 10 Mb region.

EXAMPLE 5

The following procedure is provided as yet another application of the novel mapping method disclosed herein.

Generating a Map of Repetitive Elements

Presently, only maps of restriction sites and probes (e.g., for RFLPs) are used for reference of DNA regions. Restriction mapping is generally performed on cloned DNA, either YACs or cosmids, or on a finite region of genomic DNA defined by a probe. Restriction mapping of megabases of DNA can only be performed practically using enzymes that recognize rare sites. This makes the mapping difficult without large contiguous YAC clones. Thus, it is useful to develop methods for mapping other defined sites within the genome to produce a reference map which is more easily generated than a restriction map.

Repetitive sequences such as Alu or L1 repeats, which are represented in the human genome at about $5 \times 10^5$ and $10^4$ copies (Schmid et al., 1982; Scott et al.), respectively, may serve to replace restriction sites as reference points in genomic maps. These repeat sites could be many kb in size, the repeats would be marked by stretches of signal on a megabase sized map. The location of specific probes could then be placed on this map in reference to the pattern of these sites to determine physical linkage.

The strategy for mapping repeats in the genome is to use the DIRVISH technique to visualize the sites of hybridization of either an Alu repeat probe or an L1 repeat probe on a region of DNA found in a radiation hybrid or YAC DNA along with a cosmid probe. Since some regions of the genome having a high density of Alu or L1 repeats and others a low density, not all regions may be mappable using both probes. In fact, regions dense with the Alu repeats are generally mutually exclusive of regions dense with line repeats (Korenber et al., 1988; Moyzis et al., 1989; Lichter et al., 1990). Therefore, nearly all regions may be suitable for one or the other repeat map. The high density of Alu repeats in the genome, about one every 10 kb on the average, suggests a very complex pattern, yet one which may be very distinctive. An Alu repeat map generated by this technique might be similar to, for example, a HindIII restriction site map in complexity, but much simpler to produce and interpret. An L1 repeat map with one repeat every 300 kb might be comparable in complexity to a SalI restriction site map.

The yeast DNA will be spread and fixed to slides, followed by hybridization with either a digoxigenin-labelled Alu or L1 repeat probe. The fluorescein detection of digoxigenin (green) was used for the probes, and the DNA will be stained blue with DAPI. The Alu repeat probe was the insert from BLUR 8 (Deininger et al., 1981). Since Alu repeats are only about 300 bp in length, the efficiency and sensitivity in detecting these sites may be limited. It may be necessary to reduce the stringency of hybridization and washing to obtain efficient hybridization to all repeats since the Alu probe is small and not all Alu repeats are identical.

A 6 kb L1 probe (Scott et al., 1987) will be employed for L1 repeat hybridizations. This probe is large enough for sensitive detection using the DIRVISH technique. If all 6 kb is hybridized to a site then a fluorescent signal of about 2 µm or greater is expected. However, since not all L1 repeats are full-length, they will not hybridize to the entire 6 kb, and thus smaller signals would appear. The stringency of hybridization and washing may need to be reduced for the L1 repeat probe, since not all L1 repeats are identical.

Figure 11:
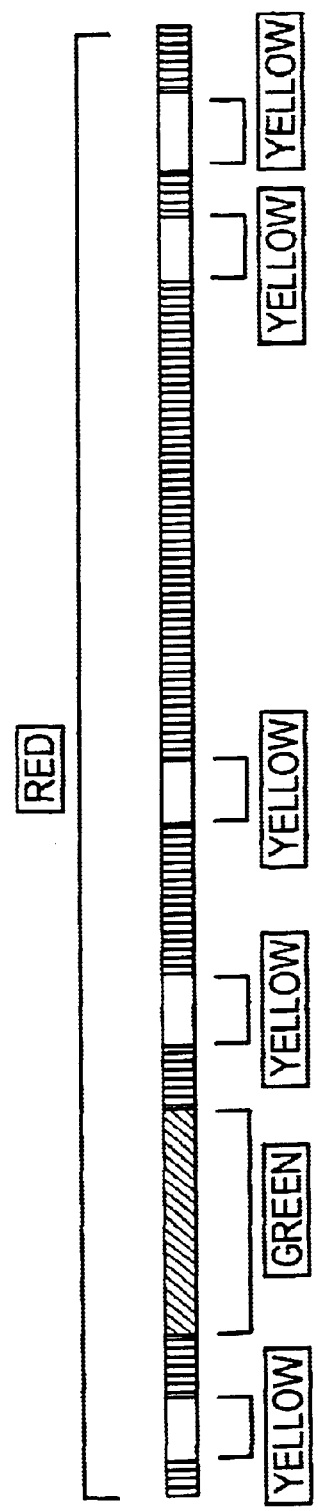
FIG. 11 is a diagrammatic illustration of the unexpected results of the simultaneous hybridization of a cosmid and repetitive sequence probes to a YAC.

The ultimate goal in creating a repeat map is to determine the location of a specific probe on the map. Therefore, a biotin-labelled cosmid probe, either 1F10 or 7D5 (pre-annealed with total human DNA) may be hybridized to the target DNA simultaneously with the digoxigenin-labelled repeat probe. A compromise in stringency of hybridization may be necessary for this experiment. The repeats would appear as green fluorescence, the cosmid probe as red. FIG. 11 is a diagram of the possible appearance of the simultaneous hybridization of a cosmid and repeat probes to a YAC.

Since the cosmid contains a vector sequence which is likely to be contained within the YAC vector (at the YAC's telomeres), there are red fluorescent signals marking the ends of the YAC. This indicates that the YAC is intact.

A third type of repetitive sequence, referred to as alpha repeats, are found in centromeric regions of chromosomes, and can be unique to one or a few chromosomes (Greig et al., 1989; Waye et al., 1986). The mapping of these regions is frequently difficult due to the sparsity of interspersed unique sequences. Mapping alpha repeats in centromeric regions using the DIRVISH technique may help bridge the gap between the two arms of the chromosome and also provide a reference for probes that are near tot he centromeric region.

EXAMPLE 6

The disclosed DIRVISH DNA mapping techniques allows quick mapping of large stretches of uncloned DNA. The following example illustrates use of the disclosed method to accomplish such mapping.

DIRVISH DNA Mapping of Uncloned Large Chromosomal DNA

The ultimate goal for the DIRVISH DNA mapping technique is to map the position of probes on DNA strands directly from the genome, thus eliminating the need for cloning (e.g., in YACs) and restriction enzyme digests for mapping. DIRVISH DNA mapping of genomic DNA has the potential to be more accurate than YAC mapping, since genomic DNA is not subject to the rearrangements often seen in YAC clones.

In addition to a repeat map near the probes, a repeat map for an entire chromosome is possible from sorted chromosomes. If the average size of DNA strands were 1 Mb (1 field of view under maximum magnification), then, for example, chromosome 17 (~85 Mb) would theoretically take a minimum of 85 different analyses to cover the entire chromosome and at least 300 different analyses to ensure covering a large majority of the chromosome. The analysis of significantly larger DNA strands, conceivably as large as 5 Mb, will reduce the number of total analyses needed. It is likely that the ends of the DNA strands will be at random locations and thus there will be overlap between strands of different individual chromosome 17s. Connecting the maps of all of these strands will rely on alignment of identical overlapping repeat map patterns and on the physical linkage of specific hybridized probes.

DNA strands that span the junction between the centromere and the two chromosomal arms may be identified by alpha repeat hybridization in conjunction with Alu or L1 repeat hybridizations. The ends of the chromosome are expected to appear as strands with a single discrete end points in reference to a specific probe or a repeat map. These strands can be confirmed to have a telomeric ends by hybridization with the repeat (TTAGGG)n, found at telomeres (Moyzis et al., 1988).

EXAMPLE 7

The new method of DIRVISH DNA mapping was compared with a FISH probe of a DNA spread obtained by standard methods. The results showed that the signal sensitivity was 10-fold greater with the DIRVISH method.

Figure 13:
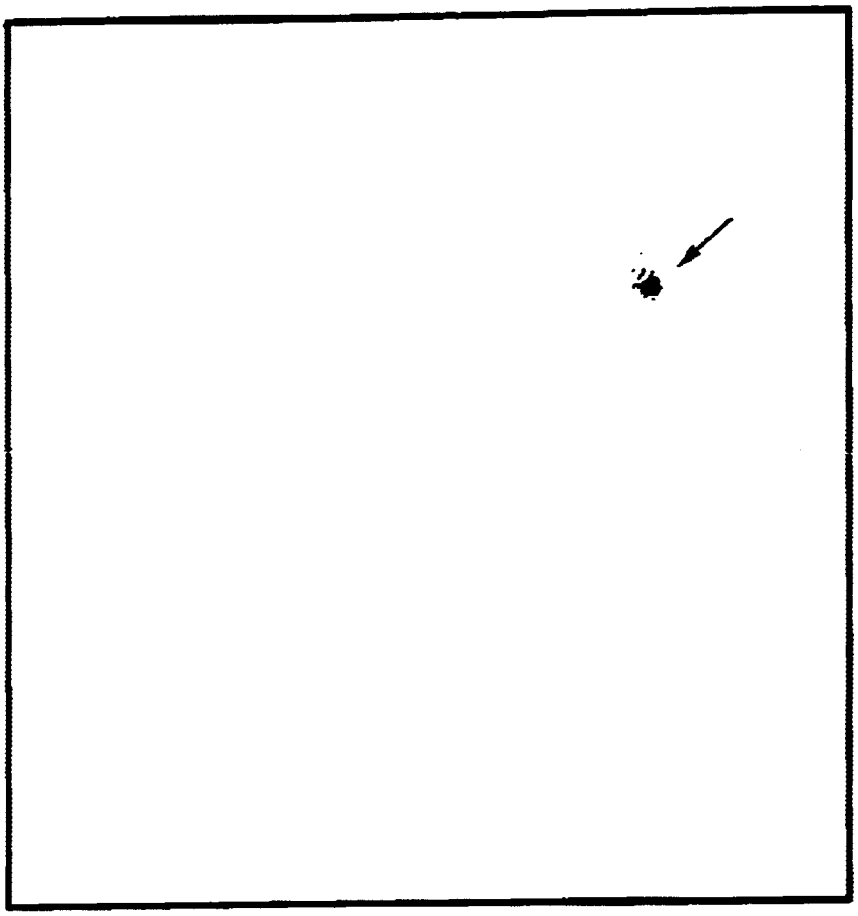
FIG. 13 shows a nuclear (DNA) spread prepared by conventional methods labelled with the same probe hybridized to the extended DNA of FIG. 12.
Figure 12:
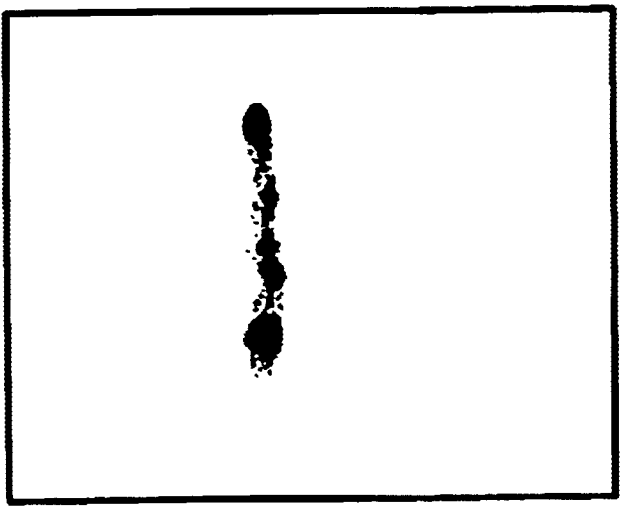
FIG. 12 shows a cosmid with a 38 kb insert labelled with biotin hybridized to extended DNA prepared in accordance with the present invention and as described in Example 1.

FIG. 12 shows a cosmid with a 38 kb insert labelled with biotin hybridized to DNA prepared by the gravitational streaming method of Example 1. FIG. 13 shows the same probe used to hybridize with a DNA spread. The biotinylated probe was detected with avidin-fluorescein plus a biotinylated antiavidin antibody amplification. The length of the DIRVISH string is approximately 4.7 $\mu$m. The ball-shaped signal shown in FIG. 13 (see arrow) represents the specific probe signal and is approximately 0.7 $\mu$m in diameter. The total amount of fluorescent signal is higher when the DNA is stretched as shown in FIG. 12, rather than when the probe is hybridized to the DNA in the spread (FIG. 13).

The average density of fluorescent signal over the length of the DIRVISH strings (FIG. 12) was comparable to or higher than the density of FISH signals (FIG. 13). This represents a 10-fold increase in signal when the DNA is extended rather than spread.

Figure 14:
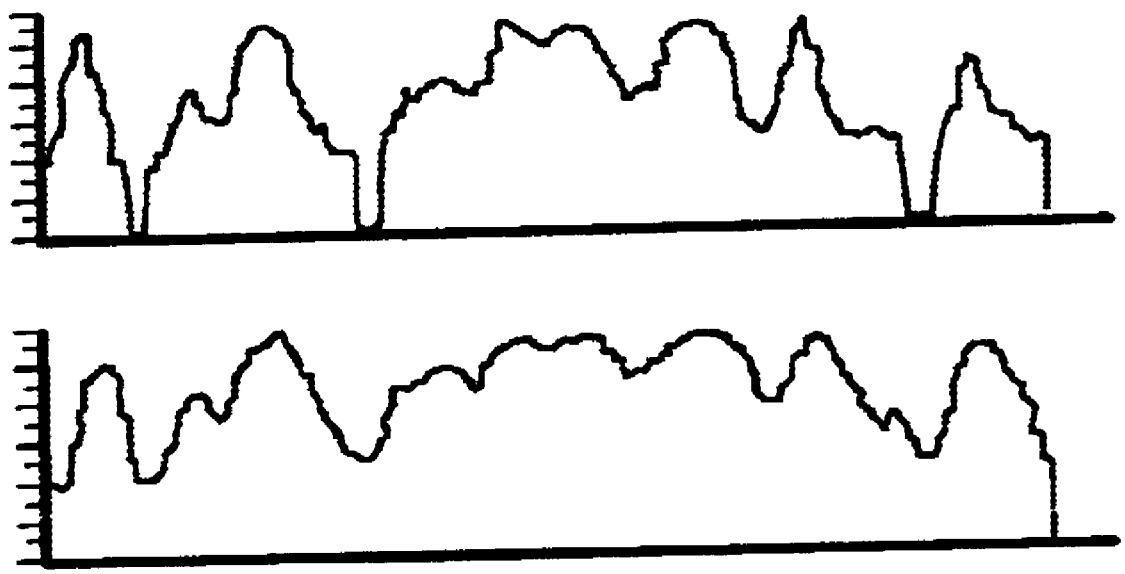

The intensity through DIRVISH strings of signal was variable. A scan through the signal strings using digital scanning produced reproducible patterns representing fingerprints specific for each probe used. FIG. 14 shows two scans through two DIRVISH signal strings from the probing with a cosmid. The patterns are strikingly-similar. The fingerprint patterns generated are specific for the region of DNA being probed, allowing immediate identification of a gene or DNA region.

While the compositions and methods of this invention have been described in terms of preferred embodiments, it will be apparent to those of skill in the art that variations may be applied to the methods described herein without departing from the concept, spirit and scope of the invention. More specifically, it will be apparent that one might map positions of repeats on DNA strands to determine repeat polymorphisms between individuals, determination of the structure of very large genes such as the Duchenne's Muscular Dystrophy gene, use of probes from NotI linking or jumping libraries to place NotI sites on a DIRVISH DNA map or detection of site-specific breaks. All such similar applications, as well as other variations in producing extended or super-extended DNA apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques, and/or compositions employed herein.

Botstein, D, White, R L, Skolnick, M and Davis, R W. (1980) *Am. J. Hum. Genet.* 32: 314–331.

Burke, D T, Carle, G F and Olson, M V. (1987) *Science* 236: 806–812.

Burmeister, M and Lehrach, H. (1986) *Nature* 324: 582–585.

Cangiano, G, Ameer, H, Waterston, R and La Volpe, A. (1990) *Nuc. Acids Res.* 18: 5077–5081.

Coulson, A, Waterston, R, Kiff, J, Sulston, J and Kohara, Y. (1988) *Nature* 335: 184–186.

Deininger, P L, Jolly, D J, Rubin, C M, Friedman, T and Schmid, C W. (1981) *J. Mol. Biol.* 151: 17–33.

Evans, G A and Lewis, K A. (1989) *Proc. Natl. Acad. Sci. USA* 86: 5030–5034.

Glazer, A N, Peck, K and Mathies, R A. (1990) *Proc. Natl. Acad. sci. USA* 87: 3851–3855.

Goss, S J and Harris, H. (1975) *Nature* 255: 680–684.

Greig, G M, England, S B, Bedford, H M and Willard, H F. (1989) *Am. J. Hum. Genet.* 45: 862–872.

Huberman, J A and Riggs, A D. (1966) *Proc. Natl. Acad. Sci. USA* 55: 599–606.

Korenberg, J R and Rykowski, M C. (1988) *Cell* 53: 391–400.

Leach, R J, Thayer, M J, Schafer, A J and Fournier, R E K. (1989) *Genomics* 5: 167–176.

Lehninger, A. L. in Biochemistry, Worth Publishers, Inc., New York, N.Y., 1970, pp 635–658.

Lichter, P, Ledbetter, S A, Ledbetter, D H and Ward, D C. (1990) *Proc. Natl. Acad. Sci. USA* 87: 6634–6638.

Lichter, P, Tang, C J, Call, K, Hermanson, G, Evans, G A, et al. (1990) *Science* 247: 64–69.

Litt, M. and Luty, J A. (1989) *Am. J. Hum. Genet.* 44: 397–401.

Moyzis, R K, Buckingham, J M, Cram, L S, Dani, M, Deaven, L L, et al. (1988) *Proc. Natl. Acad. Sci. USA* 85: 6622–6626.

Moyzis, R K, Torney, D C, Meyne, J, Buckingham, J M, Wu, J R, et al. (1989) *Genomics* 4: 273–289.

Nakamura, Y, Leppert, M, O'Connell, P, Wolff, R, Holm, T, et al. (1987) *Science* 235: 1616–1622.

Paulson, J R and Laemmli, U K. (1977) *Cell* 12: 817–828.

Pinkel, D, Straume, T and Gray, J W. (1986) *Proc. Natl. Acad. Sci. USA* 83: 2934–2938.

Poustka, A, Pohl, T M, Barlow, D P, Frischauf, A M and Lehrach, H. (1987) *Nature* 353: 353–355.

Ruddle, F H, Chapman, V M, Ricciuti, F, Murnane, M, Klebe, R, et al. (1971) *Nature New Biology* 232: 71–73.

Sasaki, M S and Norman, A. (1966) *Exp. Cell Res.* 44: 642–645.

Schmid, C W and Jelinek, W R. (1982) *Science* 216: 1065–1070.

Schwartz, D C and Koval, M. (1989) *Nature* 338: 520–522.

Scott, A F, Schmeckpeper, B J, Abelrazek, M, Comey, C T, O'Hara, B, et al. (1987) *Genomics* 1: 113–125.

Stallings, R L, Torney, D C, Hildebrand, C E, Longmire, J L, Deaven, L L, et al. (1990) *Proc. Natl. Acad. Sci. USA* 87: 6218–6222.

Trask, B, Pinkel, D and van den Engh, G. (1989) *Genomics* 5: 710–717.

Viskochil, D, Buchberg, A M, Xu, G, Cawthon, R M, Stevens, J, et al. (1990) *Cell* 62: 187–192.

Wallace, M R, Fountain, J W, Brereton, A M and Collins, F S. (1989) *Nuc. Acids Res.* 17: 1665–1677.

Wallace, M R, Marchuk, D A, Andersen, L B, Letcher, R, Odeh, H M, et al. (1990) *Science* 249: 181–186.

Waye, J S and Willard, H F. (1986) *Mol. Cell. Biol.* 6: 3156–3165.

Weber, J L and May, P E. (1989) *Am. J. Hum. Genet.* 44: 388–396.

Wiegant, et al. (1992) *Human Molecular Genetics*, 1(8):587–591.

Windle, B, Draper, B W, Yin, Y, O'Gorman, S and Wahl, G M. (1991) *Genes Dev.* 5, 160–174 (1991).

Yagle, M K, Parruti, G, Xu, W, Ponder, B A and Solomon, E. (1990) *Proc. Natl. Acad. Sci. USA* 87: 7255–7259.

What is claimed is:

1. A method of producing super-extended DNA, comprising the steps:

streaming a DNA sample over a supporting surface to provide a DNA extended to an interkilobase pair distance that exceeds about 0.34 $\mu$m.

2. The method of claim 1 wherein the DNA is obtained from cellular DNA.

3. The method of claim 2 wherein cellular DNA is released from the cell by contacting said cell with a detergent.

4. The method of claim 2 wherein the cellular DNA is released from a cell by mechanical disruption, sonication, enzymatic degradation, hypotonic bursting, heat shock or cold shock.

5. The method of claim 1 wherein the supporting surface is a glass surface.

6. The method of claim 1 wherein the streaming is accomplished gravitationally.

7. The method of claim 6 wherein the gravitational streaming is accomplished by tilting the supporting surface at an angle of between about 15° to about 90° horizontal.

8. The method of claim 1 wherein the DNA is fixed to the surface with paraformaldehyde, formaldehyde, glutaraldehyde, alcohol, acid or heat.

9. The method of claim 1 wherein the DNA is fixed to the surface with a methanol/acetic acid mixture.

10. The method of claim 2 further comprising treating the cellular DNA with a protein denaturant.

11. A super-extended DNA that has an interkilobase pair distance greater than about 0.34 $\mu$m.

12. The super-extended DNA of claim 1 that has an interkilobase pair distance of about 0.65 $\mu$m.

13. A superextended DNA produced by the method of claim 1.

14. A super-extended DNA prepared by gravitationally streaming the DNA over a supporting surface wherein the DNA is stretched to an interkilobase pair distance of greater than about 0.34 $\mu$m.

* * * * *

UNITED STATES PATENT AND TRADEMARK OFFICE
CERTIFICATE OF CORRECTION

PATENT NO.    : 6,638,715 B1
DATED         : October 28, 2003
INVENTOR(S)   : Windle It is certified that error appears in the above-identified patent and that said Letters Patent is hereby corrected as shown below:

<u>Column 20,</u>
Line 42, delete "claim 1" and insert -- claim 11 --.
Line 44, delete "superextended" and insert -- super-extended --.

Signed and Sealed this

Twenty-third Day of March, 2004

JON W. DUDAS
*Acting Director of the United States Patent and Trademark Office*